(12) United States Patent
Heuer (10) Patent No.: US 10,687,868 B2
(45) Date of Patent: Jun. 23, 2020

(54) EXTENSION DEVICE FOR A BONE ANCHOR, IN PARTICULAR FOR A PEDICLE SCREW

(71) Applicant: Silony Medical International AG, Frauenfeld (CH)

(72) Inventor: Frank Heuer, Filderstadt (DE)

(73) Assignee: Silony Medical International AG, Frauenfeld (CH)

( * ) Notice: Subject to any disclaimer, the term of this patent is extended or adjusted under 35 U.S.C. 154(b) by 0 days.

(21) Appl. No.: 16/116,342

(22) Filed: Aug. 29, 2018

(65) Prior Publication Data

US 2019/0059957 A1    Feb. 28, 2019

(30) Foreign Application Priority Data

Aug. 31, 2017 (DE) ..................... 10 2017 120 110

(51) Int. Cl.
*A61B 17/70* (2006.01)
*A61B 90/00* (2016.01)

(52) U.S. Cl.
CPC ...... *A61B 17/7076* (2013.01); *A61B 17/7083* (2013.01); *A61B 17/7085* (2013.01); *A61B 17/7035* (2013.01); *A61B 2090/037* (2016.02)

(58) Field of Classification Search
CPC ............ A61B 17/7076; A61B 17/7083; A61B 17/8875; A61B 17/7032; A61B 17/7074; A61B 17/8635; A61B 17/7082; A61B 17/7037; A61B 17/8605; A61B 17/888; A61B 17/7086; A61B 17/708; A61B 17/0206; A61B 17/7085; A61B 17/7089; A61B 17/7091

USPC ............ 606/246–289, 86 A, 86 R, 86 B, 191
See application file for complete search history.

(56) References Cited

U.S. PATENT DOCUMENTS

| | | | | |
|---|---|---|---|---|
| 7,491,208 B2* | 2/2009 | Pond, Jr. | ............ | A61B 17/7082 606/104 |
| 7,666,189 B2* | 2/2010 | Gerber | ............... | A61B 17/7074 606/104 |
| 8,002,798 B2* | 8/2011 | Chin | .................. | A61B 17/7037 606/246 |
| 9,198,698 B1* | 12/2015 | Doose | .................. | A61B 17/708 |

(Continued)

FOREIGN PATENT DOCUMENTS

| WO | 2007021588 A1 | 2/2007 |
|---|---|---|
| WO | 2015145343 A1 | 10/2015 |

*Primary Examiner* — Pedro Philogene
(74) *Attorney, Agent, or Firm* — Dilworth & Barrese, LLP (57) ABSTRACT

The invention relates to an extension device (2) for a bone anchor (4), in particular for a pedicle screw having an axial longitudinal direction (16), a circumferential direction (18) concentric thereto and a radial direction (20), wherein the extension device (2) is extended in the axial longitudinal direction (16) and can be detachably fixed to the head (8) of the bone anchor (4), wherein the extension device (2) comprises two shell parts (22) that are separate from each other and extended in the longitudinal direction 16, characterized in that, the extension device further comprises a sleeve-like housing part (60) that can be slid in the axial longitudinal direction (16) onto the two shell parts (22) which are separated from each other and detachably fixed to the head of the bone anchor and, in the applied state, limits and defines a tunnel-like access (106) to the bone anchor (4) that extends in the axial direction (16).

20 Claims, 9 Drawing Sheets

(56) References Cited

U.S. PATENT DOCUMENTS

| | | | |
|---|---|---|---|
| 9,918,751 B2* | 3/2018 | Jackson | A61B 17/7008 |
| 10,159,579 B1* | 12/2018 | Reitblat | A61B 17/708 |
| 2006/0074445 A1 | 4/2006 | Gerber et al. | |
| 2017/0164985 A1* | 6/2017 | Reitblat | A61B 17/708 |

* cited by examiner

Fig. 7

EXTENSION DEVICE FOR A BONE ANCHOR, IN PARTICULAR FOR A PEDICLE SCREW

This application claims priority to German Patent Application No, 10 2017 120 110.6 filed on Aug. 31, 2017.

BACKGROUND OF THE INVENTION

The invention relates to an extension device for a bone anchor, in particular for a bone screw, in particular for a pedicle screw, in particular in minimally invasive spinal surgery, having an axial longitudinal direction, a circumferential direction concentric thereto and a radial direction, wherein the extension device is extended in the axial longitudinal direction and can be detachably fixed in the longitudinal direction to the head of the bone anchor via a radial projection of an engageable area on the head of the bone anchor in the longitudinal direction and also engages in the radial direction and is detachable at the head of the bone anchor, but is rigidly and also rotationally fixed in the longitudinal direction,
wherein the extension device comprises two shell parts that are separated from each other and extended in the longitudinal direction, each of which comprises a radial projection for engaging behind the engageable area on the head of the bone anchor,
wherein the respective shell part (22) is predominately designed to be dimensionally stable. A device of this type is known from the not-previously published patent application DE 10 2017 114273.8 of the applicant.

Extension devices of the type named above are preferably used in minimally invasive procedures, in particular for implantation of bone anchors. They are intended to keep a working channel to the bone anchor accessible during the surgical procedure, through which the surgeon can attach the bone anchor by means of additional instruments, and, if necessary, supply and attach additional implant parts and implement repositioning measures.

An extension device having two shell parts separated from each other is known, for example, from WO 2007/021588 A1. These shell parts must be attached by means of an additional mounting part on the head of the bone anchor that connects the two parts. A radial engagement of the shell parts on the head of the bone anchor does not seem to be provided.

SUMMARY OF THE INVENTION

The present invention is based on the object of further improving an extension device of the aforementioned type having two shell parts with respect to its practical applicability during the surgical procedure.

The object is achieved according to the invention by an extension device of the aforementioned type in that the extension device further comprises a sleeve-like housing part that can be slid onto the two shell parts which are separated from each other and detachably fixed to the head of the bone in the axial longitudinal direction and, in the pushed on state, limits and defines an extended, tunnel-like access to the bone anchor.

By providing the sleeve-like housing part in addition to the two shell parts removably fixed during the operation, a tunnel-shaped, delimited access channel can be achieved through which the surgeon can access the bone anchor, namely to implant the bone anchor or to apply additional implant parts or else to remove the bone anchor.

Through the use of the additional sleeve-shaped part, it can also be effectively prevented that the surrounding fabric presses the two shell parts against each other and thus narrows the access space to the bone anchor delimited by the shell parts. It also proves to be especially advantageous that the additional sleeve-shaped housing part can be slid onto the two shell parts immediately after they are applied or at a later instance during the surgical procedure at the discretion of the surgeon.

It proves to be advantageous if the sleeve-like housing part in the applied state surrounds at least 70%, preferably at least 80%, preferably at least 90% and further preferably 100% of the longitudinal extent of the two shell parts in the axial longitudinal direction. The tunnel-shaped access channel is then protected along a sufficient length against being pressed together and in other respects stabilized. It should be noted here that the two shell parts already extend over a substantial length out of the body toward the outside where constricting forces no longer have an effect. Nevertheless, it also proves to be advantageous here if the two shell parts are surrounded by the sleeve-like housing part outside the body.

It also proves to be advantageous if the sleeve-like housing part has one and preferably two projections protruding radially inward that serve as spacers between the two shell parts separated from each other and transversely distanced from the axial longitudinal direction. In this manner, the two shell parts can be held at a distance from each other specified by the spacer.

Upon further reflection, it is proposed that the sleeve-like housing be configured in such a way that the two shell parts are bent toward each other when the sleeve-like housing part is pushed transverse to the axial longitudinal direction. In this manner, a bracing of the two shell parts against the outer, sleeve-like housing part can be achieved, whereby a slight frictional engagement can also be produced that is adjustable in a suitable way such that the sliding on of the housing part can be haptically controlled.

In a further development of the present thought, it proves advantageous if the two shell parts are bent toward each other in the area proximal to the two radial projections protruding inward when the sleeve-like housing part is pushed. The aforementioned projection already serves as a spacer between the shell parts, thereby defining a support point, on which the originally intended distance of the shell parts from each other is maintained. The shell parts are thus only slightly bent toward each other proximal to this support point.

In order to bend the two shell parts slightly toward each other as described above, the sleeve-like housing part can have a run-in bevel designed radially inward against which the shell parts run, in particular in the area of their free ends if the sleeve-like housing part is pushed in the axial longitudinal direction on the shell parts.

It further proves advantageous, if at least one shell part and preferably the two shell parts can be detachably connected to the sleeve-like housing part in such a manner that the sleeve-like housing part cannot be pulled off in the proximal direction by the shell parts.

To this end, it is proposed that at least one shell part and preferably the two shell parts can be connected to the sleeve-like housing part in such a manner that the shell parts are first bent radially inward towards each other in the area proximal to their free ends and then move radially outward into a locked position with the sleeve-like housing part when the sleeve-like housing part is slid on.

To this end, it proves advantageous that the run-in bevel designed radially inward is formed from a projection or extension extending from one wall of the sleeve-like housing part and that this projection or extension can be locked to a recess that preferably extends in the axial longitudinal direction of the shell part. According to this further design concept, the bending toward each other of the shell parts when the sleeve-shaped housing part is slid on is further used to achieve a locked state of the sleeve-like housing part on one or both shell parts, namely in such a way that the sleeve-like housing part in this locked position cannot be pulled back from the shell parts in the proximal direction.

According to a further embodiment, it proves to be advantageous that the extension device has an axial abutment area with which it runs against an axial stop on at least one of the shell parts when the sleeve-like housing part is slid on, whereby a distal end position of the sleeve-like housing part is defined. In this manner, the sleeve-like housing part can be prevented from continuing to be slid onto the shell parts or the bone anchor as intended.

The sleeve-like housing part can be designed, per se, as having an essentially continuous, specifically cylindrical wall. It can also prove to be advantageous that the sleeve-like housing part has a slit in its wall that extends from a distal end in the axial longitudinal direction. This slit can help to simplify the introduction of additional implant parts such as correcting rods that connect a plurality of bone anchors to each other.

It is provided in a further embodiment that the sleeve-like housing part has a thread in its proximal end, specifically an interior thread, to which a sleeve-like locking element can be screwed, in particular screwed into. Via this locking element, a fastening or correct orientation of the free ends of the shell parts with respect to the sleeve-like housing part, can be achieved or fastened, as desired.

In an additional embodiment of this thought, it proves advantageous if the thread is an internal thread and the internal thread in the circumferential direction is provided only in an area between the two shell parts that are separated from each other and is omitted in the area of the two shell parts. This design allows the shell parts to extend with their free ends out up to the proximal end of the sleeve-like housing part or even beyond that in the proximal direction. They then extend in the circumferential direction into the thread-free interior circumferential area of the sleeve-like housing part.

It proves to be advantageous if the sleeve-like housing part is dimensioned in the axial direction in such a way that the shell parts in the axial direction project over the distal ends and/or the proximal ends of the sleeve-like housing part if the sleeve-like housing part is pushed until it is in its final end position on the shell part.

It also proves to be advantageous if the locking element in the state of being screwed to the sleeve-like housing part braces the sleeve-like housing part and the two shell parts against each other in the axial longitudinal direction. In this manner, a further detachable fastening and arrangement of the components onto each other and against each other can be achieved. In a further development of this thought, it proves to be advantageous if the locking element in the state of being screwed to the sleeve-like housing part axially runs against the proximal free ends of the two shell parts. In this manner, an axial actuating force or clamping force between the sleeve-like housing part and preferably the two shell parts can be achieved.

This can be constructively achieved in an advantageous manner if the locking element has a flange area that is extended continuously or uninterruptedly in the circumferential direction and if the locking element can rest axially against the proximal free end of at least one of the shell parts with this flange area.

In an additional development of this thought, it can be provided that the locking element has or delimits a cylindrical annular space in which the proximal free ends of the two shell parts engage during the screwing of the locking element to the housing part.

For detachable configuration of the respective shell parts on the head of the bone anchor, it proves advantageous if the respective shell portion has, in addition to its radial projection in the axial longitudinal direction, a deflectable spring element extended in the axial direction and transverse thereto, in particular essentially radially outward, wherein the spring element has a support area projecting radially inward via which the shell part can be supported at least in the axial direction against the head of the bone anchor, so that in this way the shell portion can be detachably fixed to the head of the bone anchor if the projection engages behind the engageable area on the head of the bone anchor, and that the spring element can be deflected radially outward in order to release the extension device so that its support area comes free from the head of the bone anchor and the shell part can be moved out of the engageable area on the head of the bone anchor with respect to the head of the bone anchor. As a result, an operationally secure, detachable fastening of the shell part on the head of the bone anchor can be achieved.

The subject matter of the invention is further a set of items according to claim 20 comprising an extension device and an adapter sleeve that can be directly affixed to the head of the bone anchor. It further proves advantageous if the sleeve-like housing part and the adapter sleeve have the same external diameter. In this manner, a compatibility can be realized between systems in which the extension device is made of a single adapter sleeve and systems that use two shell parts.

Additional features, details and advantages of the extension device according to the invention derive from the attached claims and from the detailed drawing and from the following description of the embodiments according to the invention.

BRIEF DESCRIPTION OF THE DRAWINGS

FIGS. 1a, b a perspective view of a bone anchor in the form of a pedicle screw and an extension device having two shell parts;

FIGS. 2a, b views of the bone anchor having the extension device according to the invention and a sleeve-like housing part;

FIGS. 3a, b views of the bone anchor having the extension device according to the invention according to FIGS. 1a, b with an additional locking element;

DETAILED DESCRIPTION

FIGS. 1-6 show an embodiment according to the invention of an extension device 2 according to the invention and its components, partially in a detachable retaining connection on a bone anchor 4 in the form of an exemplary illustrated pedicle screw. Bone anchor 4 comprises a screw shank 6 that is arranged in a polyaxially pivotable manner with respect to a U-shaped head 8 in a lateral view of pedicle screw 4. Head 8 is a so-called "long head," for example, that is designed having longer shanks 10, wherein a predetermined breaking point 12 is provided, at which the long head in its implanted state can be shortened if a head part 13 is separable. This notwithstanding, head 8 of bone anchor 4 comprises in a known manner an engageable area 14 in the form of an engageable groove that is designed on the outer circumference of head 8. Engageable area 14 of head 8 can, moreover, be designed corresponding to the disclosure in the patent application DE 10 2014 225 327.6 of the applicant, whose content is to be included in the publication of the present application.

Extension device 2 comprises an axial longitudinal direction 16, a circumferential direction 18 concentric to it and a radial direction 20 that relates equally to head 8 of bone anchor 4. Extension device 2 comprises two shell parts 22 separated from each other and extending in longitudinal direction 16 that, as an example and preferably, are designed corresponding to each other. Shell parts 22 are essentially designed rigid and torsionally stable in the sense that they are almost completely dimensionally stable, which, however, does not preclude a slight, insignificant deformability, in particular because of the length. Shell parts 22 can be detachably attached to head 8 of bone anchor 4 in a manner yet to be described and then form a working channel 24 defined between them, through which the surgeon can gain access to the bone anchor 4 and the operational environment using additional instruments.

A respective shell part 22 is essentially designed in a dimensionally stable manner, but comprises a first spring element 28 that is extended in longitudinal direction 16 and can be deflected approximately radially outward transverse thereto. Spring element 28 in the illustrated embodiment is, for example, designed as one piece with shell part 22 and extends at its proximal end 30 in one piece into a wall 32 of shell part 22. Spring element 28 is delimited by a material-free slit 34 in wall 32 of shell part 22. Material-free slit 34 terminates with a curve at its proximal end, which causes a uniform introduction of tension into shell part 22. Spring element 28 further has a support area 36 that projects radially inward, by means of which spring element 28 and thus shell part 22 can be supported in axial longitudinal direction 16 against head 8 of bone anchor 4. This support area 36 is arranged in longitudinal direction 16, for example, proximal to a radial projection 38 of shell part 22. Radial projection 38 is designed in circumferential direction 18 in the form of an inward-projecting rib that also has an extension in the proximal direction in order to be able to engage into engageable area 14 on the head of the bone anchor; The extension of radial projection 38 in circumferential direction 18 can be seen best in FIG. 1*d*. Radial projection 38 in the exemplary embodiment illustrated here according to FIG. 1 has a central break 40 so that spring 28 can extend distally in longitudinal direction 16 through radial projection 38. It could also end before radial projection 38. In the area that is distal with respect to radial projection 38, spring element 28 comprises in the exemplary case an engagement area 42 protruding inward that can engage in an engagement recess 44 on head 8 of bone anchor 4 and can create an additional positively locked connection between shell part 22 and bone anchor 4. Spring element 28 is further designed so that it has a taper or constriction 46 in the area of central break 40 of radial projection 38, meaning it is designed narrower there in the circumferential direction.

Figures 1A, 1B:
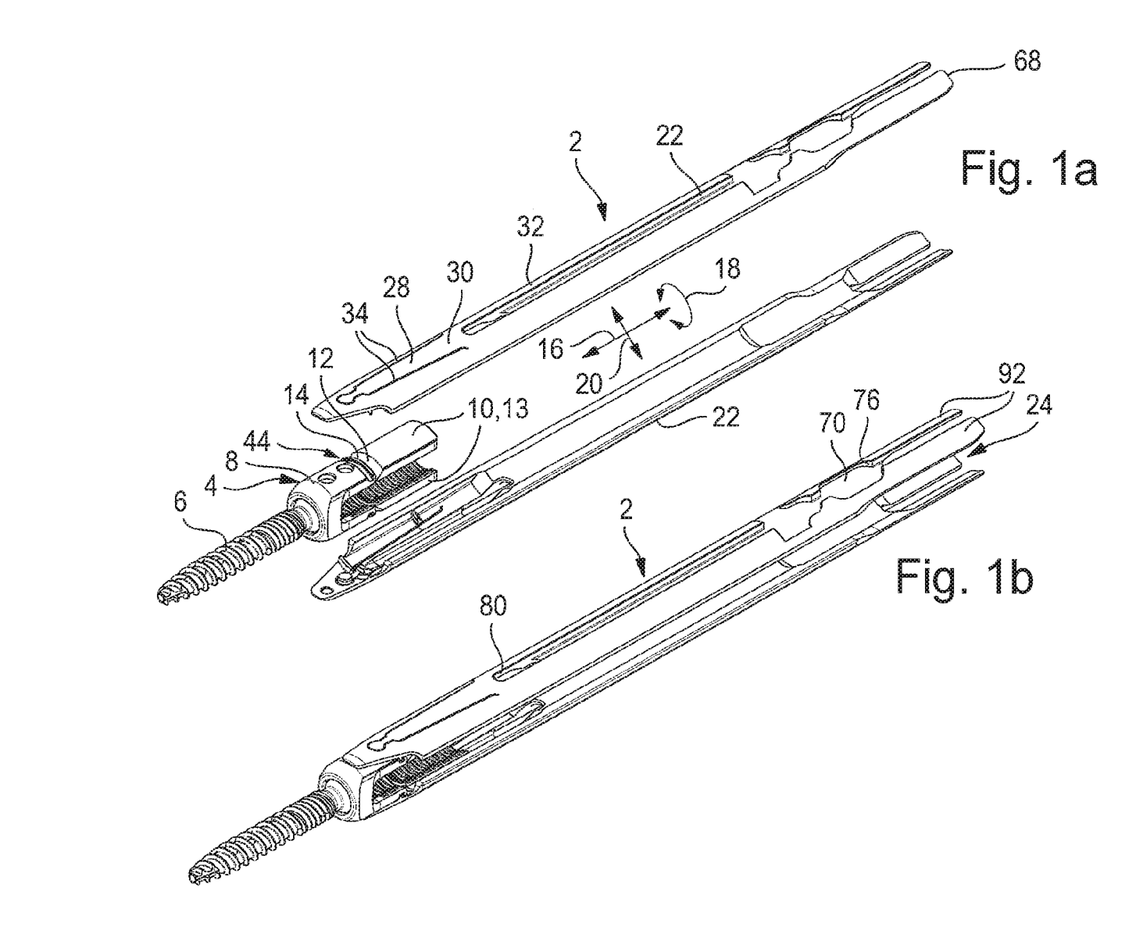
Figure 1C:
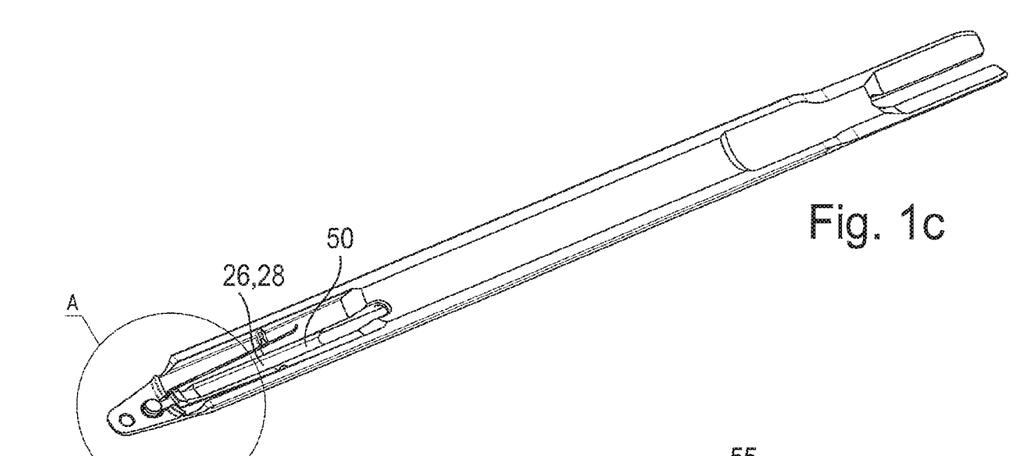
FIGS. 1c, d a view of the shell parts.
Figure 1D:
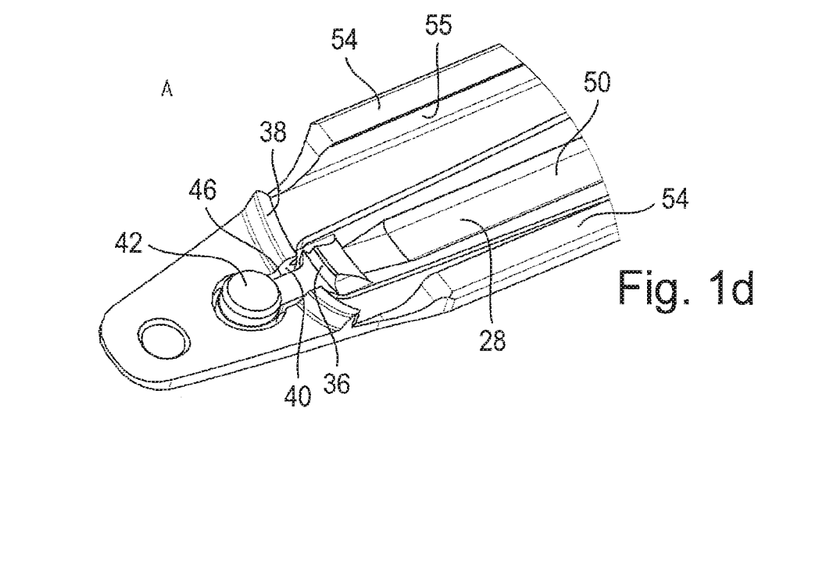

As described above, corresponding shell part 22 is held on head 8 of bone anchor 4 in a detachably yet positively locked manner with respect to all degrees of freedom in such a way that it hooks behind engageable area 14 of head 8 of bone anchor 4 in longitudinal direction 16 and in radial direction 20 by means of its radial projection 38 and supports itself in the opposite direction with its support area 36 supported against head 8, as can be seen best in FIGS. 1*a*, *b*. In the aforementioned embodiment, spring element 28 further engages into engagement recess 44 on head 8 with its distal engagement area 42. It can be seen from FIG. 3*b* that respective shell part 22 has two longitudinal edge areas 54 drawn inward via which it rests against shank 10 of head 8 of bone anchor 4 with lateral support surfaces 55 of opposing sides in circumferential direction 18. Shell portion 22 thus engages shank 10 essentially at least almost without play and is thus also non-rotatably held in circumferential direction 18 in addition to the effect of the engaging elements.

Overall, a positive operative connection is hereby created with respect to all degrees of freedom that can be activated by the spring element 28 being deflected outward in radial direction 20. This can be achieved by providing access to spring element 28 via a releasing instrument (not shown). For this purpose, a channel-forming access opening 50 extending in the longitudinal direction 16 is configured on the respective shell part 22. In the exemplary illustrated case, spring element 28 has a run-in bevel 52 for the releasing instrument, namely internally on a proximal side of support area 36.

Figures 2A, 2B:
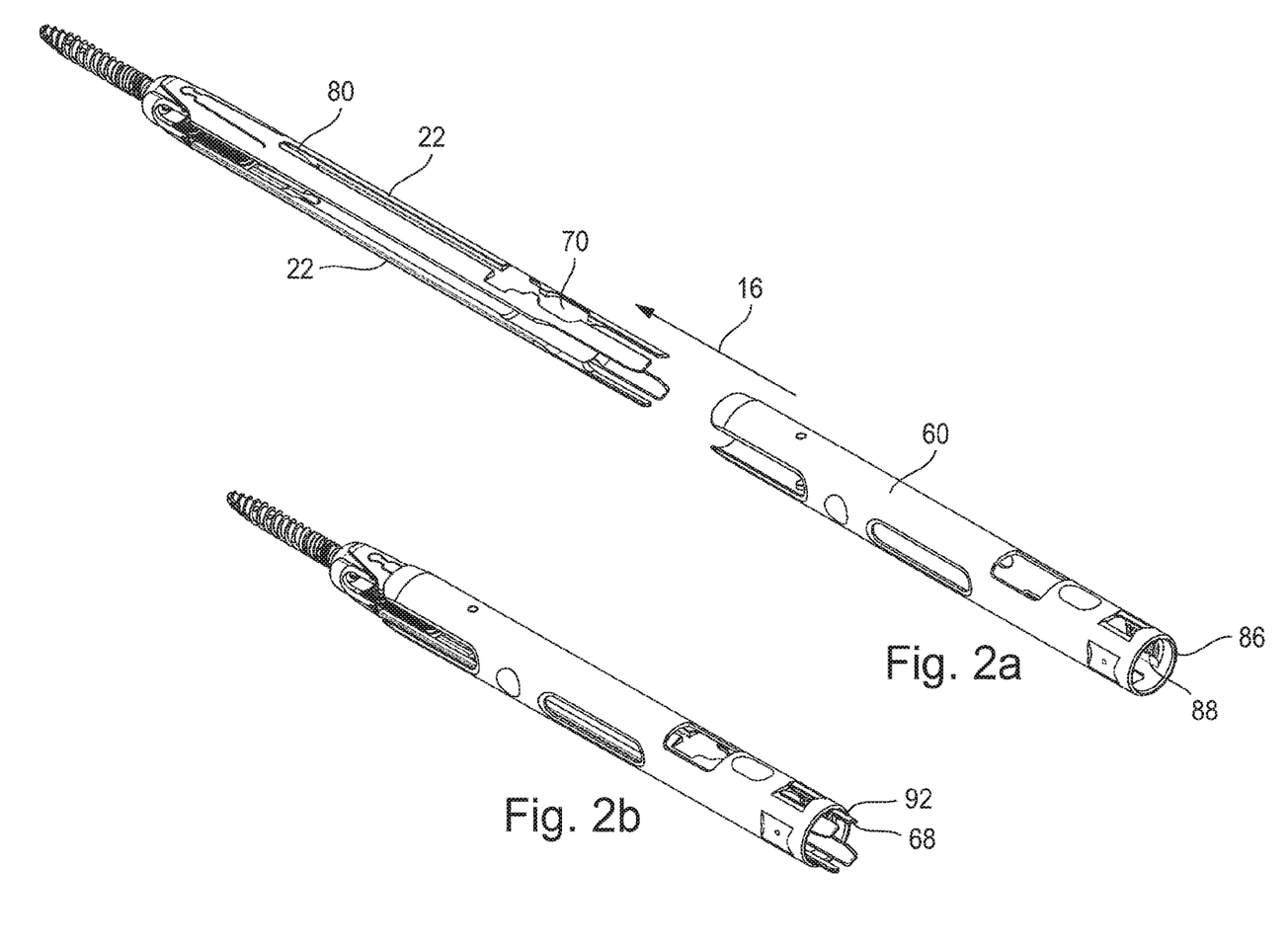
Figures 3A, 3B:
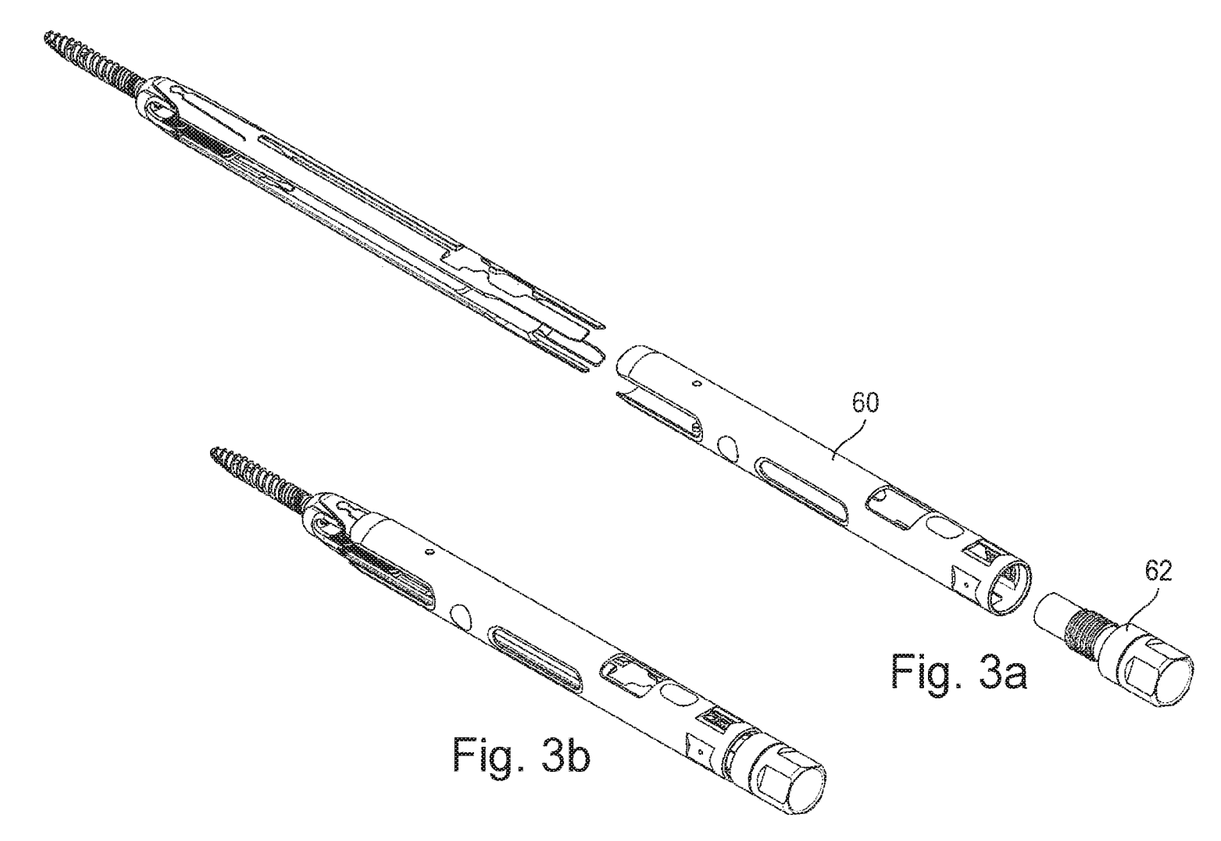
Figure 4A:
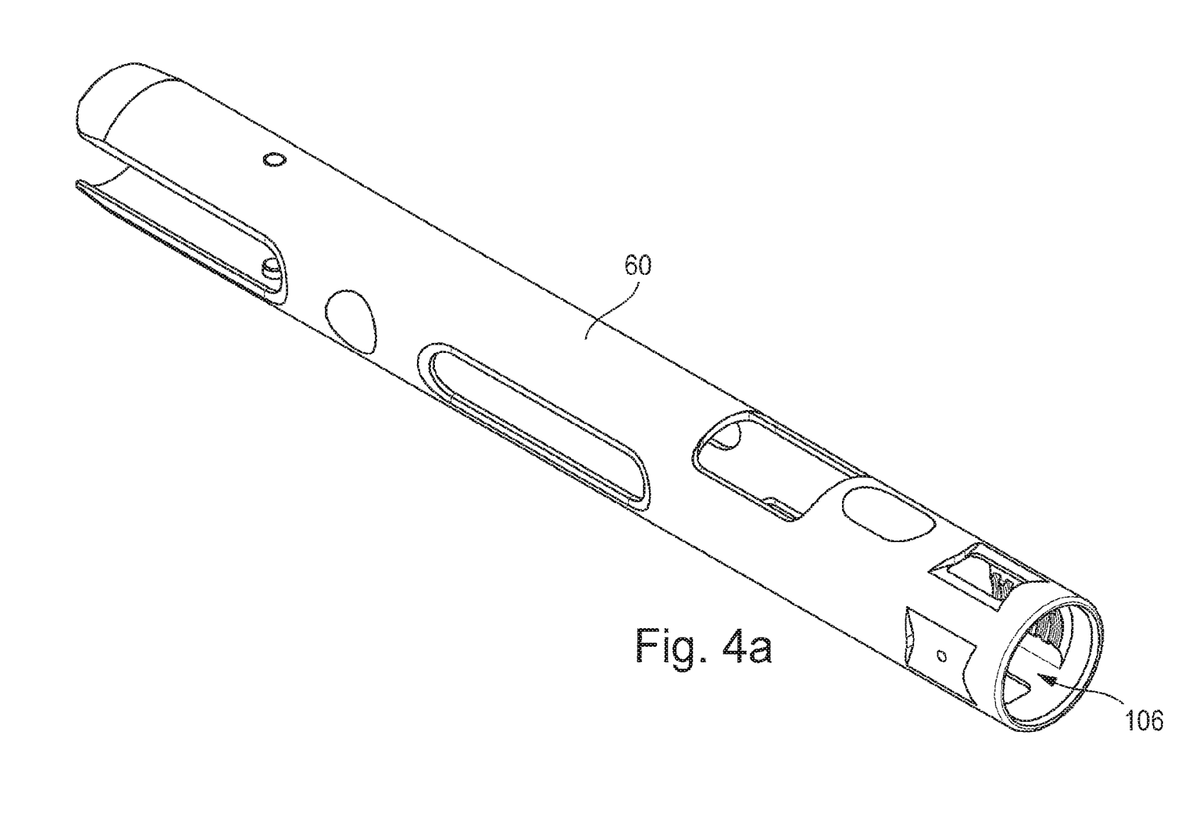
FIGS. 4a-e different views of the sleeve-like housing part.
Figure 4B:
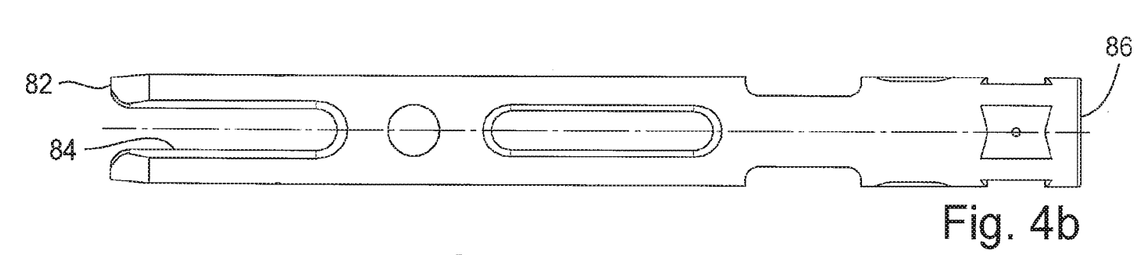
Figure 4C:
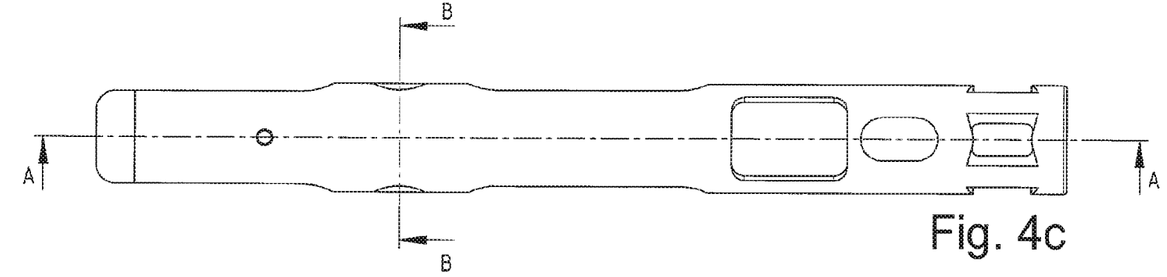
Figure 4D:
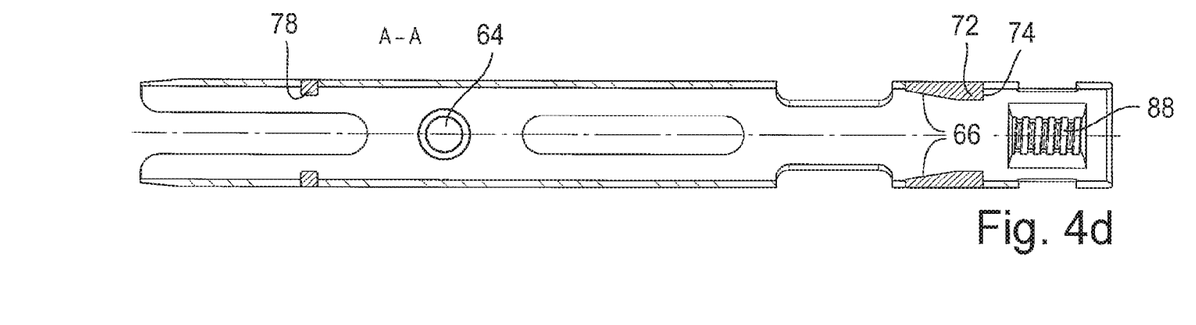
Figure 4E:
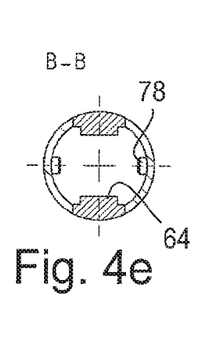
Figure 5A:
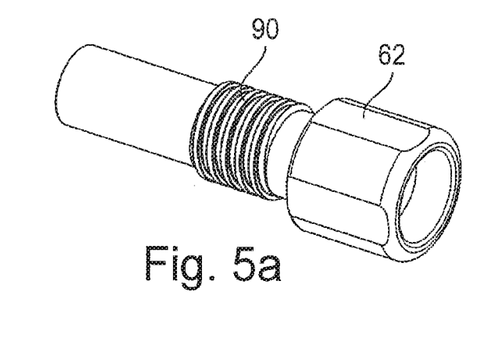
FIGS. 5a-c different views of the locking element.
Figure 5B:
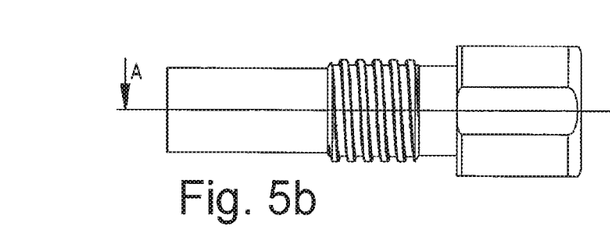
Figure 5C:
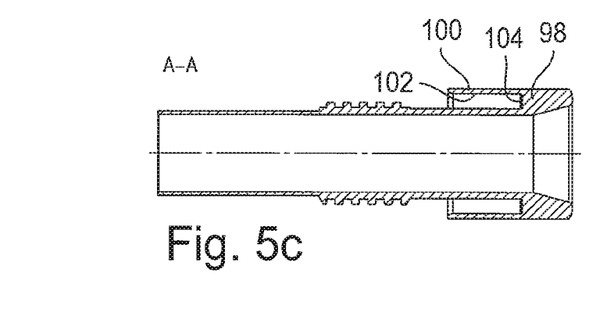

In order to increase the stability of the connection between bone anchor and the two shell parts 22 illustrated in FIGS. 1*a*) to *d*) so as to be able to execute labor-intensive repositioning maneuvers such as distraction, compression and reduction having a high mechanical stress in an operationally reliable manner, an additional sleeve-like housing part 60 is slid in the axial longitudinal direction 16 onto the two shell parts 22 fixed onto the head of the bone anchor as illustrated in FIGS. 2*a*), *b*). Sleeve-like housing part 60 is illustrated in different views in FIGS. 4*a*) to *e*). FIGS. 3*a*), *b*) and 5*a*) to *c*) illustrate an embodiment having a sleeve-like locking element 62.

Housing part 60 comprises two projections 64 protruding radially inward that have a rounded configuration so that shell parts 22 slide onto them with their free ends when housing part 60 is slid on. These projections 64 simultaneously serve as spacers between the two shell parts 22 so that an exact distance of the two shell parts 22 from each other is thereby specified. Sleeve-like housing part 60 further has, for example, two run-in bevels 66 formed radially inward (FIG. 4*d*), against which shell parts 22 run with their proximal free ends 68 if sleeve-like housing part 60 is pushed in longitudinal direction 16 onto shell parts 22. In this way shell parts 22 are first bent somewhat toward each other in the radial direction starting from their free ends 68. Because shell parts 22, as can be seen in FIGS. 1*a*), *b*), have a radial recess 70 formed on a corresponding point, shell parts 22 can snap into a locked position with sleeve-like housing part 60 if this recess 70 is radially aligned with a part 72 of housing part 60 that forms run-in bevel 66. Shell parts 22 then snap or lock again radially outwardly. In this position, part 72 then rests with a proximal axial end 74 against the wall area 76 that comes to rest there, which delimits radial recess 70 and thus prevents sleeve-like housing part 60 from being pulled back off in the proximal direction.

In order to limit the pushing of sleeve-like housing part 60 in the distal direction, sleeve-like housing part 22 has an axial abutment area 78 with which it runs against an axial stop 80 on at least one of shell parts 22 when sleeve-like housing part 60 is slid on, whereby a distal end position of the sleeve-like housing part 60 is defined.

In addition to a number of openings, sleeve-like housing part 60 has a slit 84 extending in axial direction 16 starting from its distal end 82. In the area of its proximal end 86, sleeve-like housing part 60 has an interior thread 88, into which locking element 62 with an external thread 90 can be screwed. However, interior thread 88 is not continuously formed in the circumferential direction; rather, it is only provided where shell parts 22 do not come to rest, as can be seen in FIG. 2a). Interior thread 88 thus forms to a certain extent a recess for longitudinal section 92 of shell parts 22.

Figure 6A:
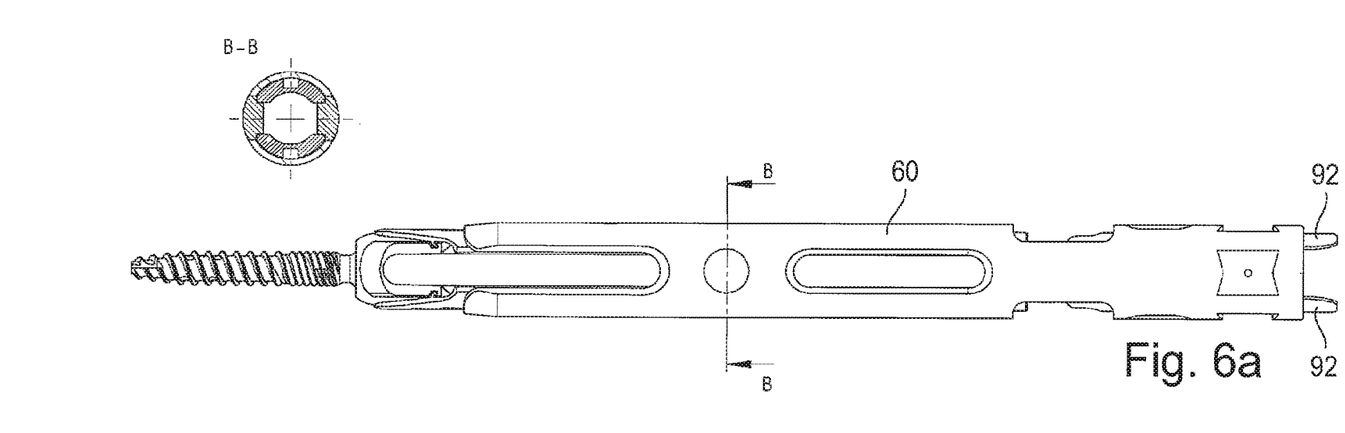
FIGS. 6a-c different side views and a longitudinal cut view of the bone anchor having an extension device according to the invention detachably affixed thereto.
Figure 6B:
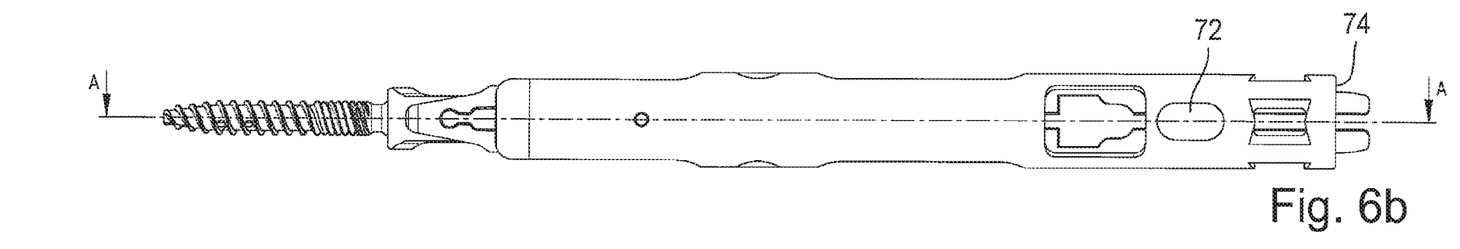
Figure 6C:
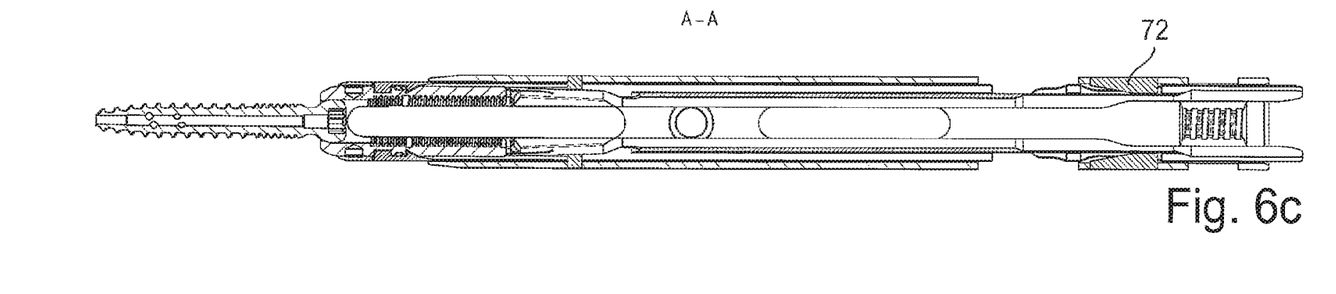

As can be seen in FIGS. 2 and 6 a) to c), shell parts 22 in the mounted state of sleeve-like housing part 60 extend in axial direction 16 outward over proximal end 74 of housing part 60. If housing part 60 based on the mounting situation shown in FIG. 6a) is pulled back off of shell ends 22 in the proximal direction, longitudinal end sections 92 of shell parts 22, which project over free end 74 of housing part 60, can thus easily be manually bent together (see arrows in FIG. 6a)) so that they reach the position illustrated in FIG. 6b). In this position, radial recess 70 of shell parts 22 comes free from part 72 that forms run-in bevel 66, whereby the latching connection is released and sleeve-like housing part 60 can be pulled back off of shell parts 22 in the proximal direction.

If sleeve-like housing part 60 is pushed onto shell parts 22 up to its distal end position (FIG. 6a)), then the locking element 62 illustrated in FIGS. 3 and 5 can be screwed in. Locking element 62 has, for its part, a sleeve-like design and comprises a flange area 38 having a cylindrical wall 100 that delimits a cylindrical annular space 102. Longitudinal end sections 92 of shell parts 22 are accommodated in this annular space 102 if locking element 62 is screwed into sleeve-like housing part 60. Finally, longitudinal sections 92 push against floor 104 of annular space 102 with their free ends. By tightening locking element 62, sleeve-like housing part 60 and shell parts 22 are consequently braced against each other axially.

Overall, the intended position of shell parts 22 and their rigid and rotationally fixed, detachable connection to the head of the bone anchor is secured and strengthened by housing part 60 that defines a housing. In addition, shell parts 22 are held in their intended position and supported in such a manner that an operating channel in the form of a tunnel-like access 106 to the bone anchor having a specified diameter and configuration is ensured.

Figure 7:
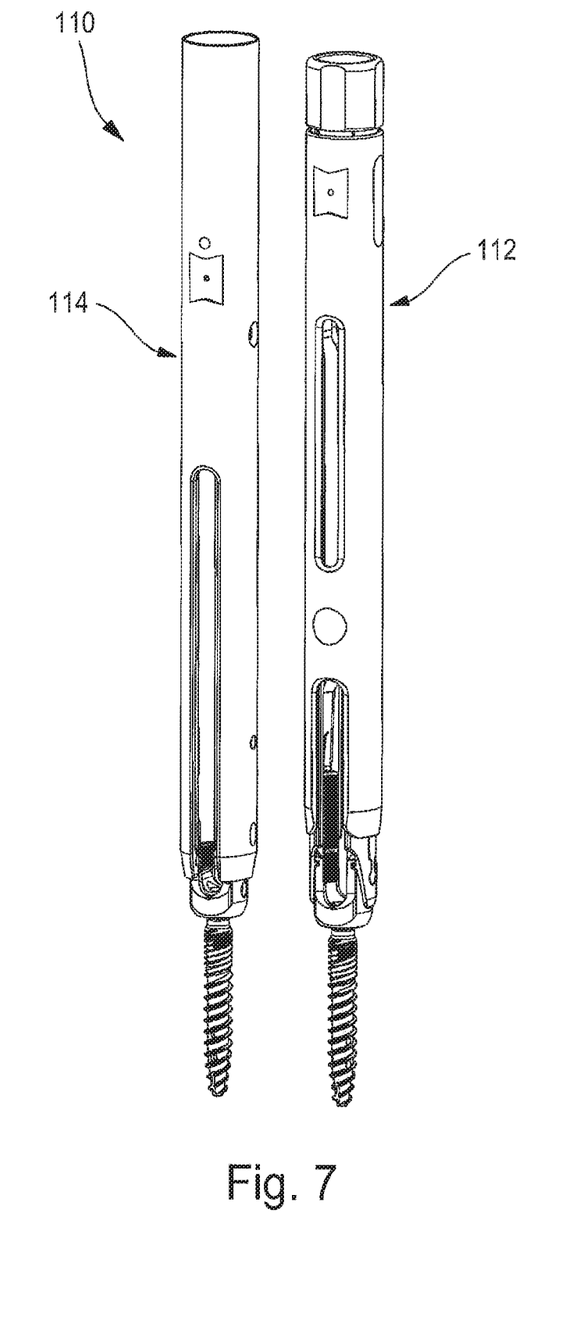
FIG. 7 a set of items comprising two different extension devices in a detachable mounting connection on a bone anchor.

FIG. 7 shows a set of items 110 comprising an extension device 112 according to the invention and an adapter sleeve 114 that can be affixed directly to the head of the bone anchor as an extension device in order to form a tunnel-like access to the bone anchor. The two extension devices are detachably affixed to the head of a pedicle screw and have essentially the same outer dimensions, in particular the same outer diameter of the cylindrical shape.

The invention claimed is:

1. An extension device (2) for a bone anchor (4), having an axial longitudinal direction (16), a circumferential direction (18) concentric thereto and a radial direction (20), wherein the extension device (2) is extended in the axial longitudinal direction (16) and, via a radial projection (38), engages behind an engageable area (14) on a head (8) of the bone anchor (4) in the longitudinal direction (16) and also in the radial direction (20) and is detachably but nevertheless rigidly and also torque proof fixable in the longitudinal direction (16), on the head (8) of the bone anchor,
   wherein the extension device (2) comprises two shell parts (22) that are separated from each other and extended in the longitudinal direction (16), each of which comprises a radial projection (38) for engaging behind the engageable area (14) on the head (8) of the bone anchor (4),
   wherein the respective shell part (22) is designed to be predominately dimensionally stable, and wherein
   the extension device further comprises a sleeve-like housing part (60) that can be slid in the axial longitudinal direction (16) onto the two shell parts (22) which are separated from each other and detachably fixed to the head of the bone anchor, and wherein the sleeve-like housing part (60) has a radially inwardly configured run-in bevel (66) against which the shell parts (22) run up if the sleeve-like housing part (60) is slid in the axial longitudinal direction (16) onto the shell parts (22) and, wherein the sleeve-like housing part (60), in the applied state, limits and defines a tunnel-like access (106) to the bone anchor (4) that extends in the axial direction (16).

2. The extension device of claim 1, wherein the sleeve-like housing part (60) in the slid-on state surrounds at least 70%, of the longitudinal extent of the two shell parts (22) in the axial longitudinal direction.

3. The extension device of claim 1, wherein the sleeve-like housing part (60) has one projection (64) protruding radially inward that serves as a spacer between the two shell parts (22) that are separated from each other and spaced apart transverse to the axial longitudinal direction (16).

4. The extension device of claim 1, wherein the sleeve-like housing part (60) is designed so that the two shell parts (22) are bent towards each other when the sleeve-like housing part (60) is slid on transverse to the axial longitudinal direction (16).

5. The extension device of claim 1, wherein the two shell parts (22) are first bent towards each other in the area proximal to the two projections (64) protruding radially inward when the sleeve-like housing part (60) is slid on.

6. The extension device of claim 1, wherein at least one shell part (22) is detachably connected to the sleeve-like housing part (60) in such a manner that the sleeve-like housing part (60) cannot be pulled off of the shell part (22) in the proximal direction.

7. The extension device according to claim 6, characterized in that the at least one shell part (22) can be connected to the sleeve-like housing part (60) in such a manner that the shell part (22) is first bent radially inward in the area proximal to its free end (68) and then goes radially outward into a locked position with the sleeve-like housing part (60) when sleeve-like housing part (60) is slid on.

8. The extension device of claim 1, wherein the run-in bevel (66) designed radially inward is formed from a projection or extension (72) extending from one wall of the sleeve-like housing part (60) and that this projection or extension (72) can be locked to a recess (70) of the shell part (22).

9. The extension device of claim 1, wherein the sleeve-like housing part (60) has an axial abutment area (78) with which it runs against an axial stop on at least one of the shell parts (22) when sleeve-like housing part (60) is slid onto the shell parts (22), whereby a distal end position of the sleeve-like housing part (60) is defined.

10. The extension device of claim 1, wherein the sleeve-like housing part (60) has a slit (84) extending in the axial longitudinal direction in its wall that extends from a distal end (82).

11. The extension device of claim 1, wherein the sleeve-like housing part (60) has a thread (88), in the area of its proximal end (86), by which a sleeve-like closure element (62) is screwable.

12. The extension device of claim 11, wherein the thread (88) is an internal thread and the internal thread in the circumferential direction (18) is provided only in an area between the two shell parts (22) that are separated from each other and is omitted in the area of the shell parts (22).

13. The extension device of claim 1, wherein the sleeve-like housing part (60) is dimensioned in the axial direction (16) in such a way that the shell parts (22) in the axial direction project over distal ends (82) and/or over proximal ends (86) of the sleeve-like housing part (60) when the sleeve-like housing part (60) is slid until it is in its final end position on the shell housing part (22).

14. The extension device of claim 11, wherein the closure element (62) in its state of being screwed to the sleeve-like housing part (60) braces the sleeve-like housing part (60) and the two shell parts (22) in the axial longitudinal direction (16) against each other.

15. The extension device of claim 11, wherein the closure element (62) in its state of being screwed to the sleeve-like housing part (60) axially runs against proximal free ends (68) of the two shell parts (22).

16. The extension device of claim 11, wherein the closure element (62) has a flange area (98) that is extended continuously or interruptedly in the circumferential direction (18) and in that the closure element (62) can rest axially against proximal free end (68) of at least one of the shell parts (22) with this flange area (98).

17. The extension device according to claim 11, wherein the closure element (62) has or limits a cylindrical annular space (102) into which proximal free ends (68) of the two shell parts (22) engage when the closure element (62) is screwed to the housing part (60).

18. The extension device of claim 1, wherein one of the respective shell parts (22) has a spring element (28) extended in the axial longitudinal direction (16), which is deflectable transverse thereto, wherein the spring element has a support area (36) projecting radially inward by means of which the shell part (22) can be supported at least in the axial longitudinal direction (16) against the head (8) of the bone anchor (4) so that, by this, the shell portion (22) is detachably fixable to the head (8) of the bone anchor (4) when the projection (38) engages behind the engageable area (14) on the head (8) of the bone anchor (4), and that the spring element (28) is capable of being deflected radially outward in order to release the extension device (2) so that its support area (36) comes free from the head (8) of the bone anchor (4), and the shell part (22) with respect to the head (8) of the bone anchor (4) is capable of being moved out of the engageable area (14) on the head (8) of the bone anchor (4).

19. A set of items comprising the extension device (2) of claim 1, and an adapter sleeve (114) for forming a tunnel-like access (24) to the bone anchor (4) that can be affixed directly to the head (8) of the bone anchor (4).

20. The set of items of claim 19, wherein the sleeve-like housing part (60) and the adapter sleeve (114) have the same outer diameter.

* * * * *